United States Patent [19]

Schutz et al.

[11] Plant 4,136

[45] Oct. 25, 1977

[54] *COLEONEMA PULCHRUM* PLANT

[75] Inventors: Murdoch Niall McIntosh; Juris E. Schutz; Murdoch Niall McIntosh, both of Sydney, Australia

[73] Assignees: Juris E. Schutz, by said Murdoch N. McIntosh; Solveiga M. Schutz; Peteris Kepitis; Elga Kepitis, by said Juris E. Schutz, all of Sydney, Australia; part interest to each

[21] Appl. No.: 721,543

[22] Filed: Sept. 8, 1976

[51] Int. Cl.[2] ..... A01H 5/00

[52] U.S. Cl. ..... Plt./54

[58] Field of Search ..... Plt./54

*Primary Examiner*—Robert E. Bagwill

*Attorney, Agent, or Firm*—Emory L. Groff, Jr.

[57] ABSTRACT

This novel mutation of *Coleonema pulchrum* is characterized by its golden foliage, pink flowers, and dwarf form.

5 Drawing Figures

The present invention comprises a new and distinct cultivar of *Coleonema pulchrum,* hereinafter referred to by the cultivar name Sunset Gold.

The new cultivar is a sport of the dwarf form of *Coleonema pulchrum,* which has been in the New South Wales, Australia nursery trade in recent years under the cultivar designation *Coleonema pulchrum compacta* or *Coleonema pulchrum nana.* The new cultivar was discovered in 1970 in New South Wales, Australia in a cultivated field of the parent cultivar, and asexual reproduction of the new cultivar by vegetative propagation of cuttings has established that the combined characteristics of the new cultivar are firmly fixed and retained through successive generations.

The new cultivar is particularly characterized by its bright golden foliage, its pink flowers, and dwarf form. The pink flowers often contain paler pink or white areas irregularly distributed on the flower petals.

The accompanying colored photographic drawings illustrate the new cultivar.

Figure 1:
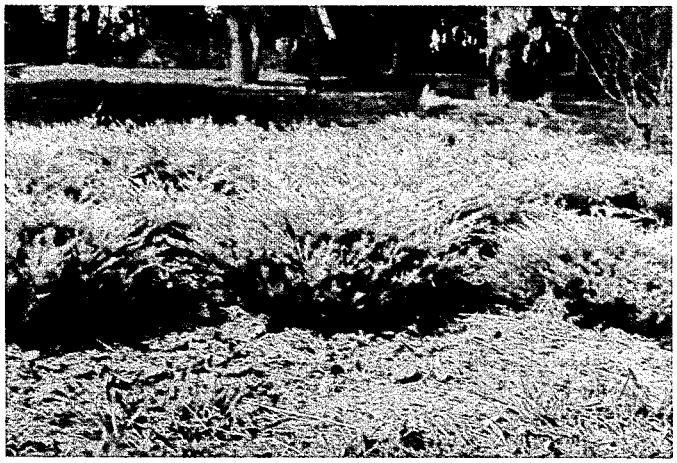
FIG. 1 shows the dwarf, compact habit of the plant. The true golden color of the plant is not well represented in this photograph because the plants are growing in semi-shade.
Figure 2:
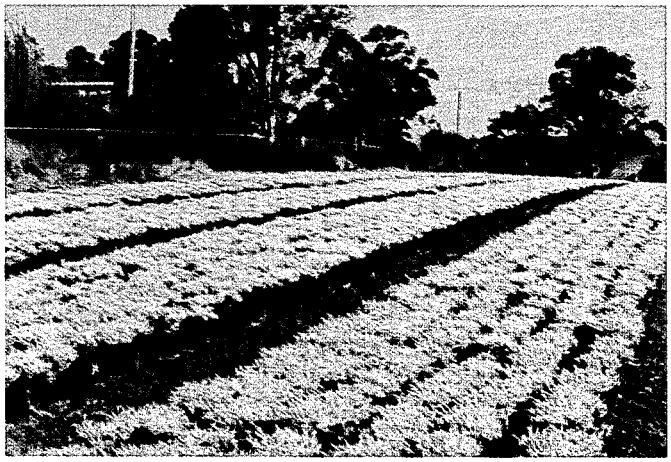
FIG. 2 shows the true autumn color of the plant in the nursery.
Figure 3:
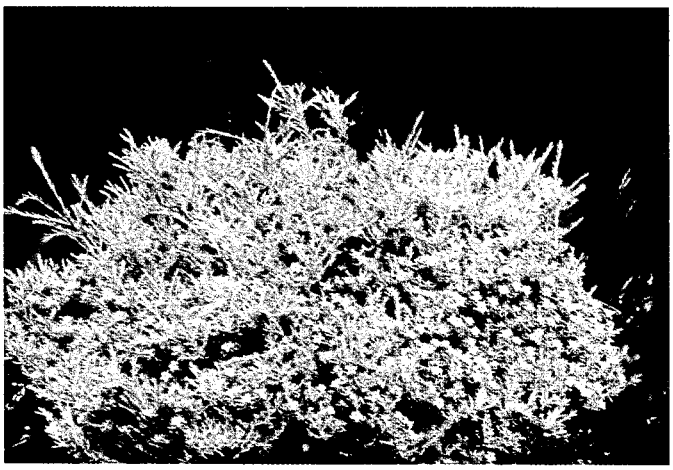
FIG. 3 shows a group of plants in flower, but does not clearly illustrate the true pink color of the flowers.
Figure 4:
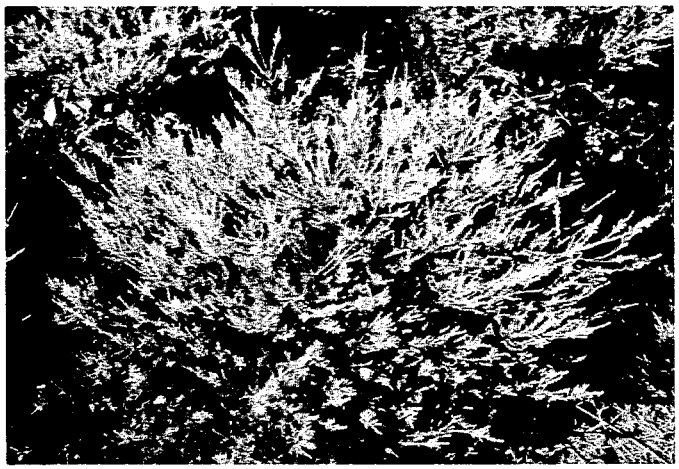

FIG. 4 also shows a group of plants, with the true golden color appearing in this photograph.

Figure 5:
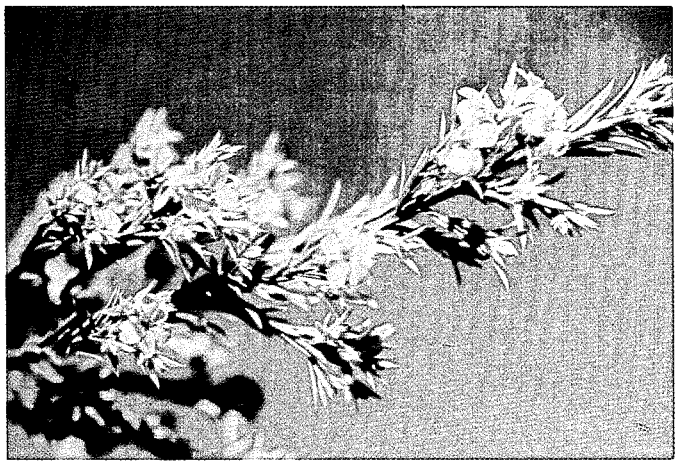

FIG. 5 is an enlarged view of several branches of the plant, with the pink flower color being clearly evident.

The following description is based on plants grown in New South Wales, Australia in an outdoor environment in accordance with normal commercial practices. Color references are to the Royal Horticultural Society Colour Chart, 1966 edition.

THE PLANT

Growth habit: A low, dense, dwarf type spreading shrub of up to 2 feet in height and 3 feet in diameter. The outer branches ascend approximately 45° from the horizontal. The main branch-tips radiate from the center of the plant at a similar angle.

Branchlets: The secondary branchlets, while the plant is young and vigorous, radiate from the main branches almost horizontally, but on more mature plants about to flower these branchlets are more erect and held closer together. Final branchlets are up to $1\frac{3}{4}''$ long.

Stems: Are at first pale pinkish-brown, soon darkening to deep reddish-brown.

Nodes: Nodes approximately 1/15 " apart.

Leaves: Spirally arranged but on the more horizontal younger branchlets the leaves on the lower side of the branchlet are turned outwards and upwards, bringing them almost into a flat plane. Leaves are up to $\frac{3}{8}''$ long and 1/16" broad, narrowly lanceolate to linear in outline, narrowing into a long fine point at the apex. Leaves are fragrant.

Foliage Color: Yellow Group 7C, becoming a more intense golden color in autumn and greener when grown in shaded conditions.

The Flowers: Flowers at apexes of short branchlets and in axils of the leaves just below the apexes. Only one flower at a time open on each branchlet.

Sepals: Similar in coloring to the leaves.

Petals: Spreading to form a flat disc up to $\frac{3}{8}''$ diameter. Petal color Red-Purple Group 68C, often with paler or white areas irregularly distributed on petals, and sometimes with deeper colored median line running most of the petal length. Petal shape is obovate to spathulate with micronate apex.

It should be noted that other botanical features of this new cultivar which are not described herein are typical of the *Coleonema pulchrum* species.

We claim:

1. A new and distinct cultivar of *Coleonema pulchrum* referred to by the cultivar name Sunset Gold and particularly characterized as to uniqueness by its dwarf growth form, golden color foliage and its generally pink flower color.

* * * * *

UNITED STATES PATENT OFFICE

CERTIFICATE OF CORRECTION

PATENT NO. : Plant 4136

DATED : October 25, 1977

INVENTOR(S) : Murdoch Niall McIntosh; Juris Edgar Schutz

It is certified that error appears in the above-identified patent and that said Letters Patent are hereby corrected as shown below:

Inventors should be shown as:

[75] Inventors: Murdoch Niall McIntosh; Juris Edgar Schutz

Assignees should be shown as:

[73] Assignees: Juris E. Schutz by said Murdoch N. McIntosh; Valdis O. Schutz, Solveiga M. Schutz, Peteris Kepitis; Elga Kepitis by said Juris E. Schutz all of Sydney, Australia; part interest to each.

Signed and Sealed this

*Seventh* Day of *August 1979*

[SEAL]

*Attest:*

*Attesting Officer*

LUTRELLE F. PARKER

*Acting Commissioner of Patents and Trademarks*